United States Patent
Tulchinsky et al.

(10) Patent No.: US 10,023,685 B2
(45) Date of Patent: Jul. 17, 2018

(54) EPOXY RESIN COMPOSITIONS

(71) Applicant: Dow Global Technologies LLC, Midland, MI (US)

(72) Inventors: Michael L. Tulchinsky, Midland, MI (US); William J. Kruper, Jr., Sanford, MI (US); Tzu-Chi Kuo, Midland, MI (US); David C. Molzahn, Midland, MI (US); Mark F. Sonnenschein, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/125,372

(22) PCT Filed: Feb. 26, 2015

(86) PCT No.: PCT/US2015/017653
§ 371 (c)(1),
(2) Date: Sep. 12, 2016

(87) PCT Pub. No.: WO2015/138128
PCT Pub. Date: Sep. 17, 2015

(65) Prior Publication Data
US 2017/0073458 A1   Mar. 16, 2017

Related U.S. Application Data

(60) Provisional application No. 61/951,749, filed on Mar. 12, 2014.

(51) Int. Cl.
| C08G 59/00 | (2006.01) |
| C08G 59/22 | (2006.01) |
| C07D 303/04 | (2006.01) |
| C07D 303/22 | (2006.01) |
| C08G 59/68 | (2006.01) |
| C09D 163/00 | (2006.01) |

(52) U.S. Cl.
CPC ......... *C08G 59/223* (2013.01); *C07D 303/04* (2013.01); *C07D 303/22* (2013.01); *C08G 59/68* (2013.01); *C09D 163/00* (2013.01)

(58) Field of Classification Search
None
See application file for complete search history.

(56) References Cited

U.S. PATENT DOCUMENTS

| 3,336,241 A | 8/1967 | Shokal |
| 3,781,244 A | 12/1973 | Vargiu et al. |
| 4,847,394 A | 7/1989 | Schuster |
| 5,530,147 A | 6/1996 | Wettling et al. |
| 5,614,646 A | 3/1997 | Wettling et al. |
| 6,130,344 A | 10/2000 | Hara et al. |
| 2004/0176549 A1 | 9/2004 | Bottcher et al. |

(Continued)

FOREIGN PATENT DOCUMENTS

| CN | 101203300 A | 6/2008 |
| EP | 1637526 A1 | 3/2006 |

OTHER PUBLICATIONS

International Search Report; International Application No. PCT/US2015/017653; International Filing Date Feb. 26, 2015; dated Aug. 5, 2015; 3 pages.

(Continued)

*Primary Examiner* — Ana L Woodward
(74) *Attorney, Agent, or Firm* — Karl E. Stauss; Cantor Colburn LLP

(57) ABSTRACT

A novel byproduct compound having the following chemical formula B:

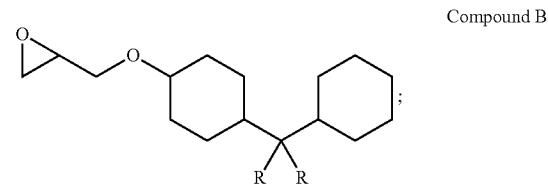

Compound B wherein R is hydrogen or $CH_3$; a composition including an admixture of: (A) a product having the following chemical formula A:

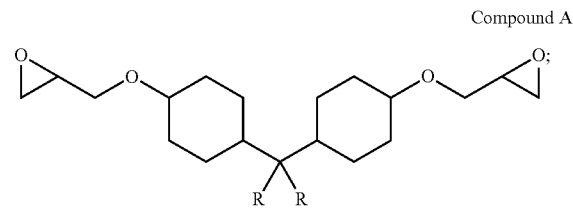

Compound A wherein R is hydrogen or $CH_3$; and (B) the above novel byproduct compound having the chemical formula B; and a composition including a reaction product of: (a) an aromatic epoxy resin; (b) hydrogen; (c) a catalyst; and (d) a solvent; wherein the reaction product produced is a cycloaliphatic epoxy resin admixture of the combination of (i) the above product having the chemical formula A and (ii) the novel byproduct compound having the chemical formula B; wherein the above product having the chemical formula A includes at least a cis-cis isomer, a cis-trans isomer, and a trans-trans isomer; and the novel byproduct compound having the chemical formula B includes at least a cis isomer and a trans isomer.

9 Claims, 7 Drawing Sheets

(56) References Cited

U.S. PATENT DOCUMENTS

2006/0252911 A1* 11/2006 Takenaka ............ C07D 303/28
528/420
2008/0139728 A1 6/2008 Klopsch et al.

OTHER PUBLICATIONS

Written Opinion of the International Searching Authority; International Application No. PCT/US2015/017653; International Filing Date: Feb. 26, 2015; dated Aug. 5, 2015, 5 pages.
Morita "Cationic Polymerization of Hydrogenated Bisphenol—A Glycidyl Ether with Cycloaliphatic Epoxy Resin and Its Thermal Discoloration"; Journal of Applied Polymer Science; 2005; vol. 97; pp. 1395-1400.
Jiang "Application of Catalytic Hydrogenation in Organic Synthesis"; Chemicai Industry Press; 1987; pp. 313-320.

* cited by examiner

FIG. 5A
Major byproduct isomer (cis):
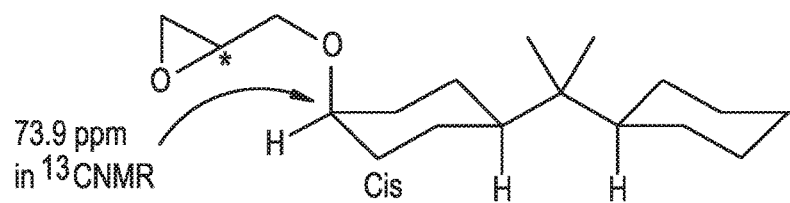
$^1$H NMR in CDCl$_3$
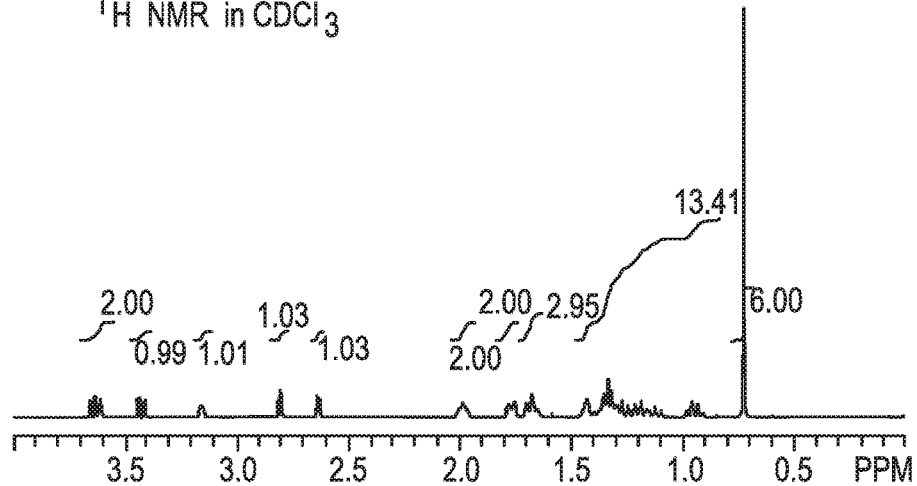

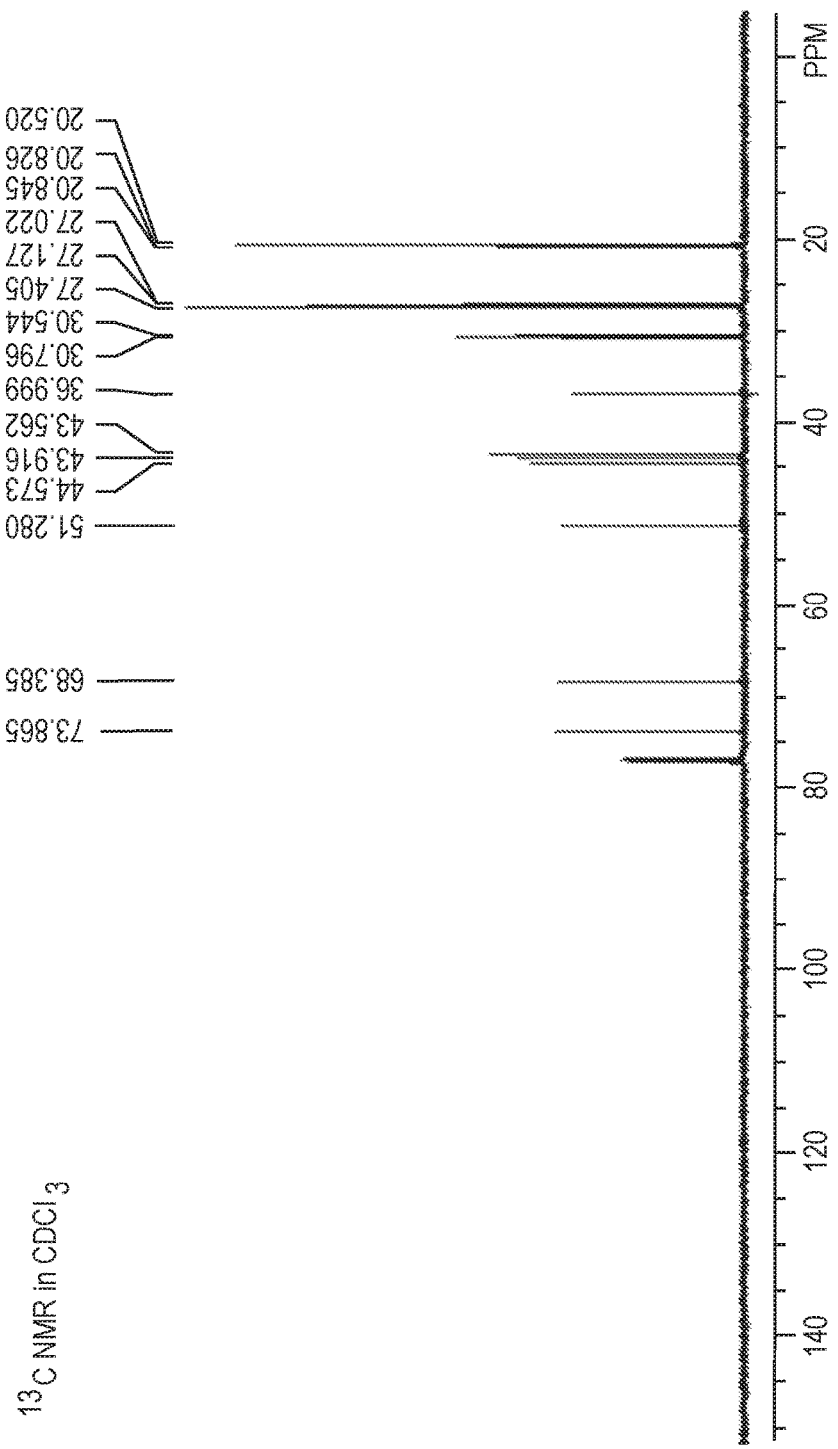

FIG. 6A
Major byproduct isomer (trans):
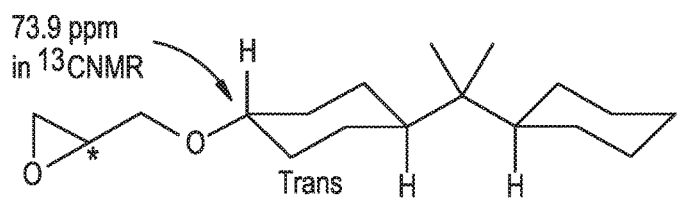
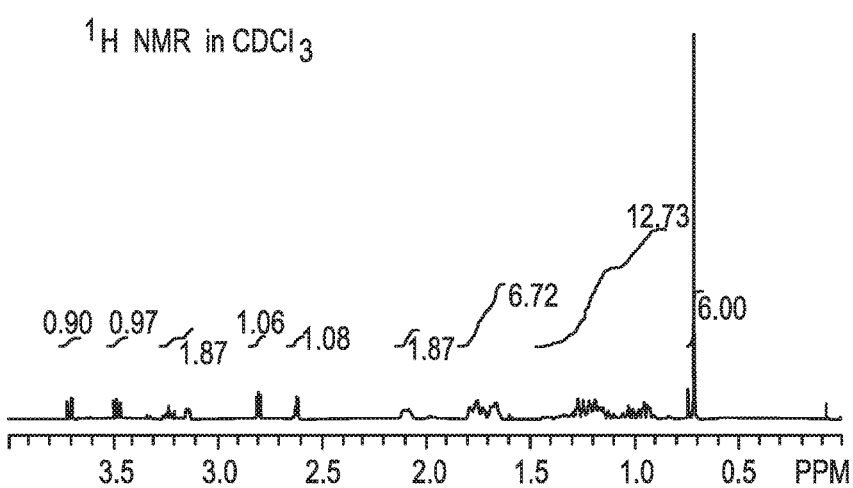

$^{13}$C NMR in CDCl$_3$

EPOXY RESIN COMPOSITIONS

FIELD

The present invention is related to epoxy resin compositions and more specifically to hydrogenated liquid epoxy resin compositions.

BACKGROUND

Catalytic hydrogenation of aromatic epoxy resins, for example diglycidyl ethers of bisphenol A, produces cycloaliphatic diepoxides. Cycloaliphatic diepoxides are useful for manufacturing weatherable coatings components in coating applications such as marine coatings, protective coatings (for example, storage tanks; bridges; industrial architecture; and the oil and gas segment), and electronic materials applications.

Currently, a few cycloaliphatic epoxy resins are available commercially based on hydrogenated bisphenol A. For example, U.S. Pat. No. 3,781,244 discloses a process for the industrial preparation of aromatics-free epoxy resins as shown in the following chemical reaction scheme, Scheme (I):

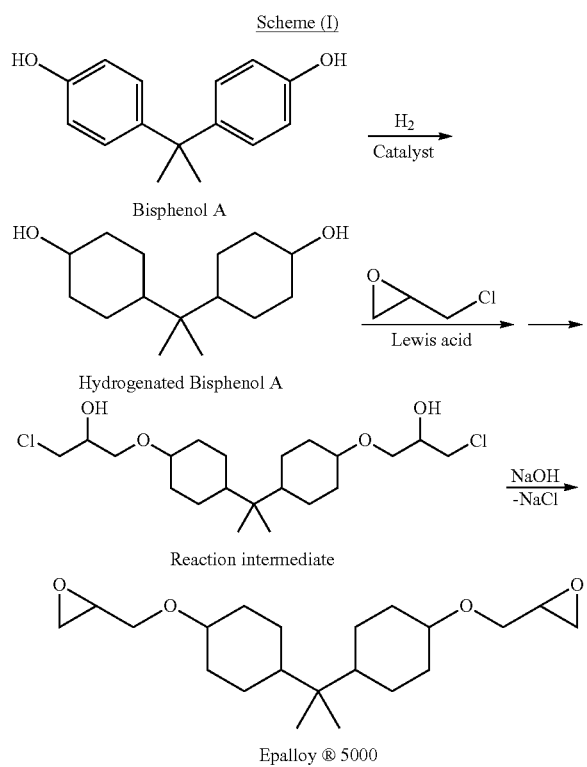

The above aromatics-free epoxy resins are commercially available under the trade names of, for example, Epalloy 5000 and Eponex 1510; and these commercial epoxy resins have long been the industry standard for use in manufacturing weatherable coatings.

Coatings made by curing the above known cycloaliphatic epoxy resins exhibit weatherability, chalk resistance and gloss retention. However, the process illustrated in above Scheme (I) produces cycloaliphatic epoxy resins having (1) a high viscosity (for example, greater than [>] 1,300 mPa-s at 25° C.), (2) a high epoxy equivalent weight (EEW) (for example, >210 g/eq), and (3) a high total chlorine content (for example, >2 wt %). And, when a curable coating composition is made from the above known cycloaliphatic epoxy resins, the resultant curable coating composition exhibits low-grade chemical resistance, adhesion and flexibility; or the resultant curable coating composition is unsuitable for certain applications especially the ones pertaining to electronic materials.

Processes for catalytic hydrogenation of bisphenol A diglycidyl ether are disclosed for example in U.S. Pat. Nos. 3,336,241; 4,847,394; 5,530,147; 5,614,646; and 6,130,344; and U.S. Patent Application Publication No. 20040176549. However, the above prior art lacks recipes for producing a high quality cycloaliphatic epoxy resin product, for example, the above known processes do not provide a product having a viscosity lower than 1,300 mPa-s at 25° C., an EEW lower than 210 g/eq, and a chlorine content lower than 1 wt %. For example, U.S. Pat. No. 3,336,241 discloses a process for direct catalytic hydrogenation of bisphenol A diglycidyl ether having an EEW of 170.4 g/eq, in the presence of a rhodium or a ruthenium catalyst, to produce a hydrogenated epoxy resin having an EEW of 256 g/eq as described in Example 1 of U.S. Pat. No. 3,336,241. The EEW of 256 g/eq of the cycloaliphatic epoxy resin product disclosed in U.S. Pat. No. 3,336,241, suggests a retention of only 69 percent (%) epoxy groups upon hydrogenation of bisphenol A diglycidyl ether starting material.

The above prior art process suffer from several disadvantages including for example: (1) the process produces a product with a high viscosity (for example, >1,300 mPa-s at 25° C.) and/or a high chlorine content (for example, >2 wt %); (2) the process involves three steps; (3) the hydrogenated reaction intermediate reacts with epichlorohydrin less selectively than its aromatic precursor, resulting in a large amount of residual chlorine from the formed byproducts.

It would be advantageous in the industry to prepare a hydrogenated epoxy resin composition product with enhanced properties, such as, for example, a product having a viscosity, of for example ≤1,000 mPa-s at 25° C., without having to use diluents or solvents resulting in improved product processability.

SUMMARY

The present invention is directed to a new composition of matter, and in particular, a new epoxy resin composition exhibiting several beneficial properties. One preferred embodiment includes a cycloaliphatic epoxy resin composition prepared by catalytic hydrogenation of an aromatic diepoxide. Some of the advantageous properties exhibited by the cycloaliphatic epoxy resin composition product of the present invention include, for example, a viscosity lower than 1,300 mPa-s at 25° C., an EEW lower than 210 g/eq, and a chlorine content lower than 1 wt %.

For example, the cycloaliphatic epoxy resin of the present invention can be prepared as illustrated by the following reaction scheme, Scheme (II):

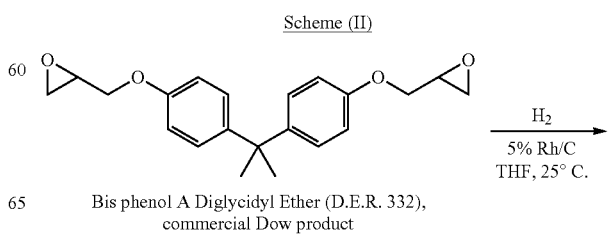

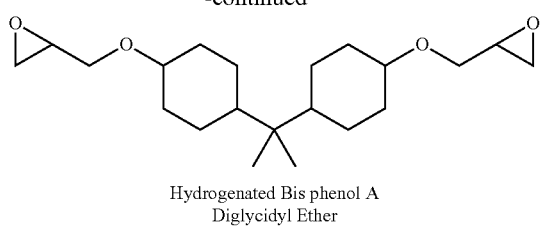

Hydrogenated Bis phenol A Diglycidyl Ether

In one embodiment, specific parameters are used in the above hydrogenation process, including for example a particular catalyst (e.g., a rhodium (Rh) on carbon catalyst), catalyst loading, solvent, substrate concentration, temperature, and pressure; to produce a cycloaliphatic epoxy resin having a low viscosity, low EEW and low total chlorine content.

One preferred embodiment of the present invention includes a hydrogenated composition such as a cycloaliphatic epoxy resin composition which comprises a reaction product of: (a) an aromatic epoxy resin, (b) hydrogen, (c) a metal catalyst, and (d) a solvent.

Another embodiment of the present invention is directed to a catalytic hydrogenation process for producing the above cycloaliphatic epoxy resin such as a cycloaliphatic diglycidyl ether via direct catalytic hydrogenation of an aromatic epoxy resin.

Some of the advantages of the process for making the cycloaliphatic epoxy resin composition product of the present invention include, for example, carrying out the reaction at temperatures of from about 20° C. to about 40° C. with a retention of the epoxy functionality of >88% and production of specific epoxy byproducts which serve as diluents and reduce the product viscosity Still another embodiment of the present invention is directed to a curable composition of matter including (i) the above cycloaliphatic epoxy resin compound reaction product and (ii) at least one curing agent compound.

Yet another embodiment of the present invention is directed to a thermoset prepared from the above curable composition.

Still other embodiments of the present invention include a process for preparing the above curable composition and a process for preparing the above thermoset product from the cycloaliphatic epoxy resin composition of the present invention for use in various applications such coatings applications.

BRIEF DESCRIPTION OF THE DRAWINGS

For the purpose of illustrating the present invention, the drawings show a form of the present invention which is presently preferred. However, it should be understood that the present invention is not limited to the embodiments shown in the drawings.

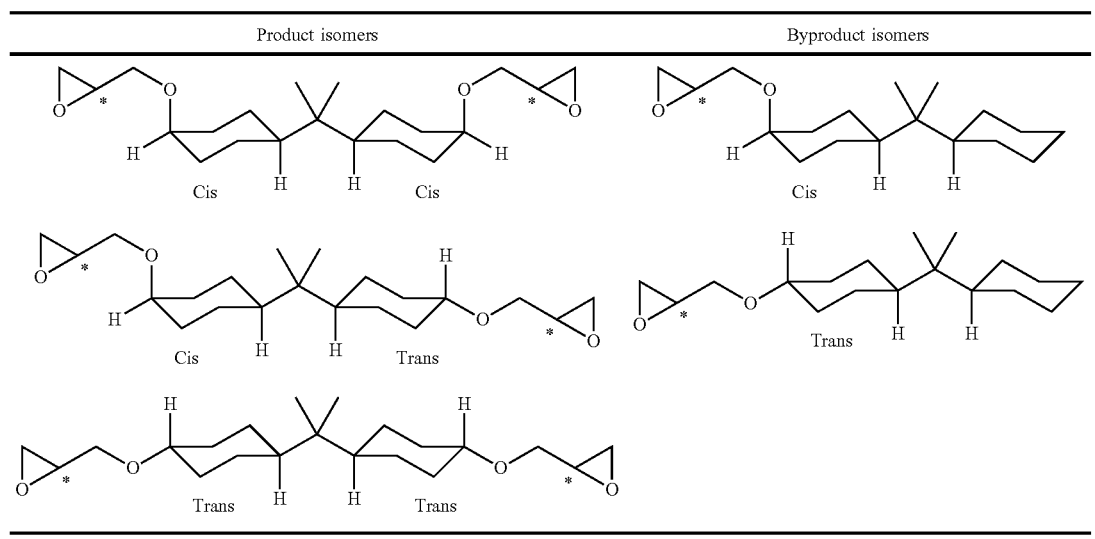

Figure 2:
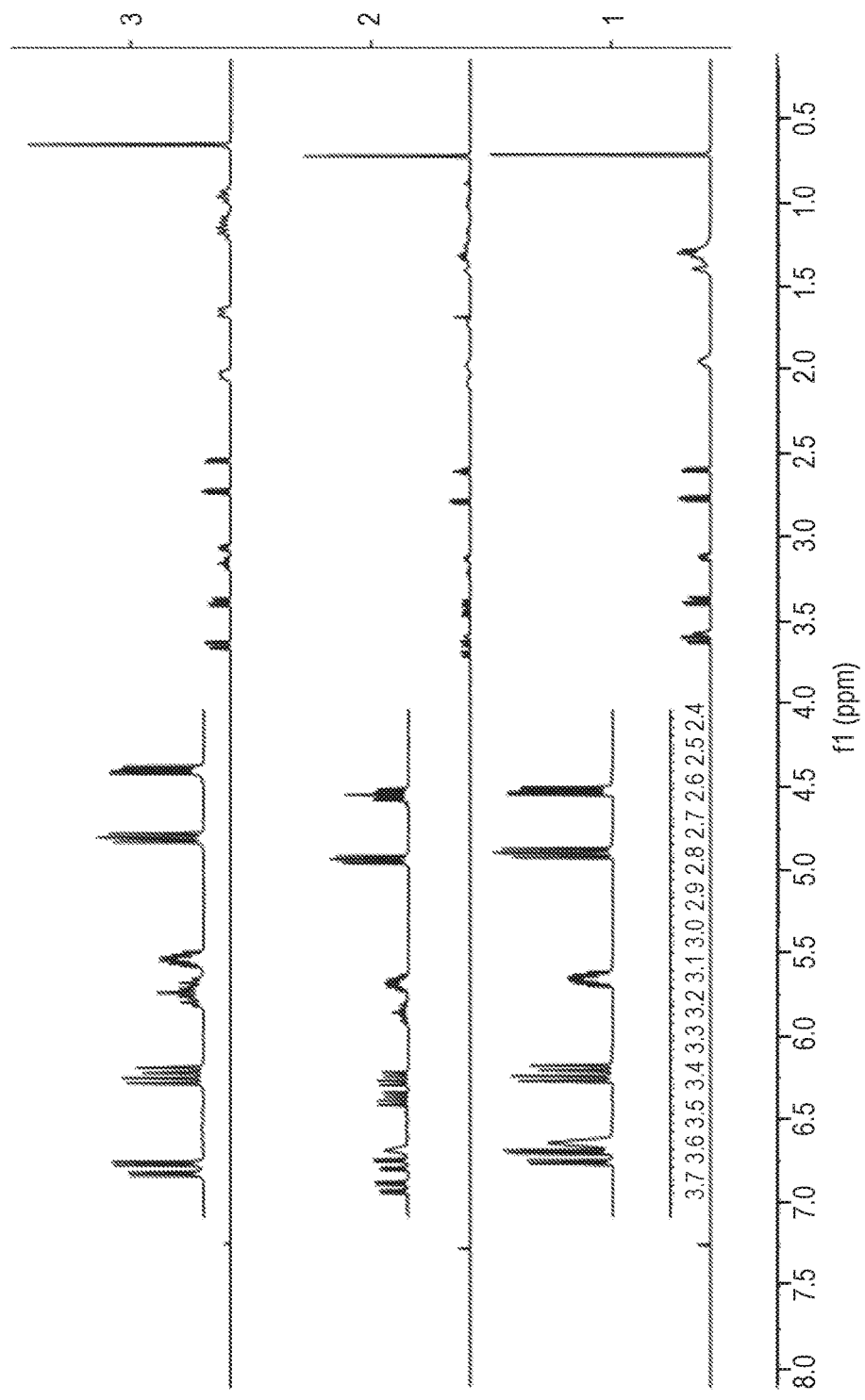

FIG. 2 is graphical illustration of $^1$H NMR spectra for three isomers of hydrogenated bisphenol A diglycidyl ether: 1-cis-cis, 2-cis-trans, and 3-trans-trans isomers.

Figure 3:
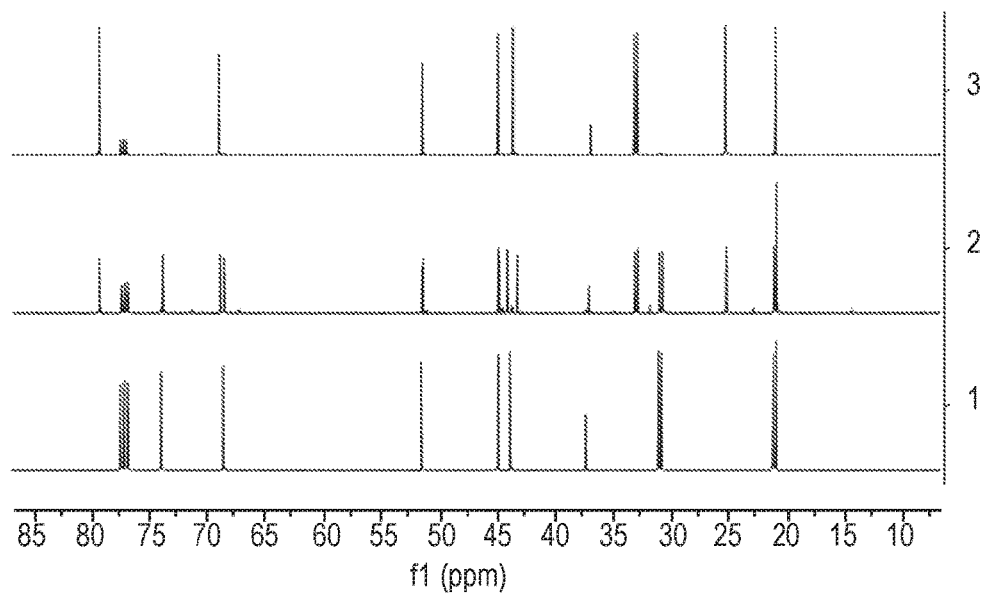

FIG. 3 is graphical illustration of $^{13}$C NMR spectra for three isomers of hydrogenated bisphenol A diglycidyl ether: 1-cis-cis, 2-cis-trans, and 3-trans-trans isomers.

Figure 4:
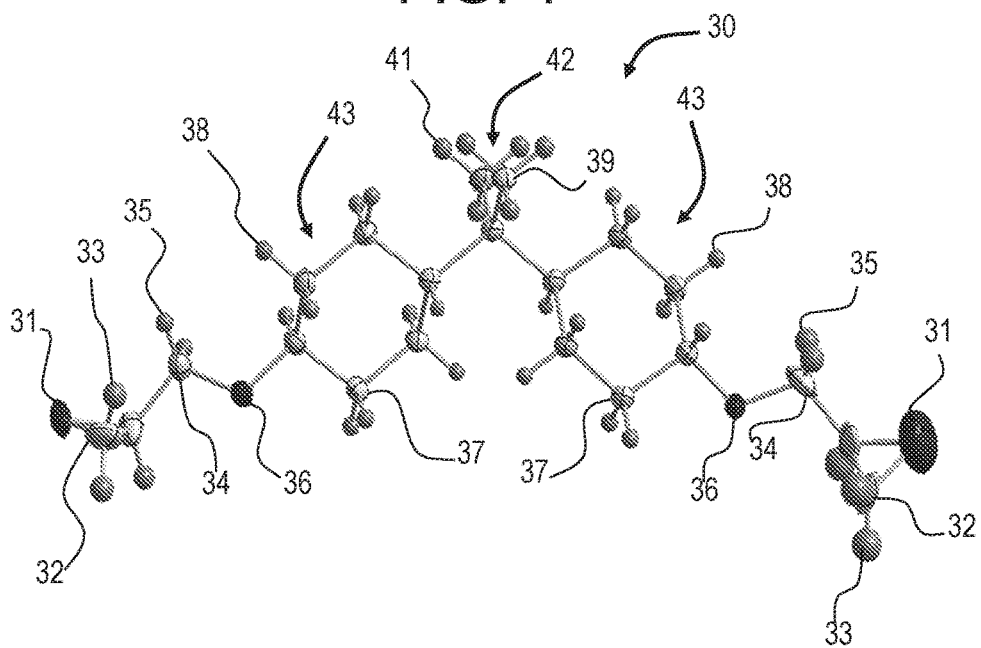

FIG. 4 is an illustration of a model molecular structure showing a perspective view of the molecular structure of a trans-trans isomer of hydrogenated bisphenol A diglycidyl ether.

FIG. 5*a* is graphical illustration of the $^1$H NMR in CDCl$_3$ and the $^{13}$C NMR in CDCl$_3$ of the major and minor byproducts.

FIG. 5*b* is graphical illustration of the $^1$H NMR in CDCl$_3$ and the $^{13}$C NMR in CDCl$_3$ of the major and minor byproducts.

FIG. 6*a* is graphical illustration of the $^1$H NMR in CDCl$_3$ and the $^{13}$C NMR in CDCl$_3$ of the major and minor byproducts.

Figure 6B:
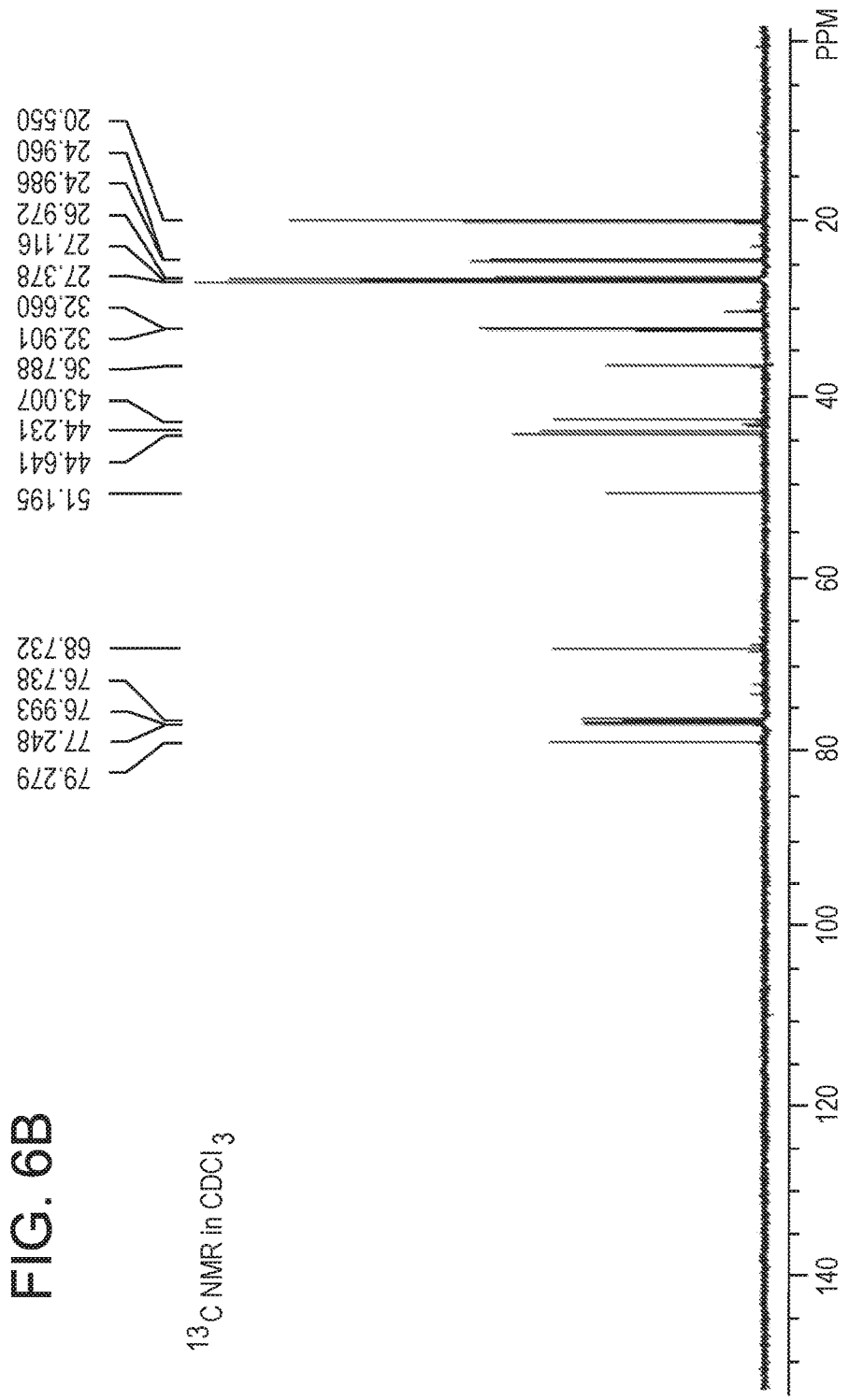

FIG. 6*b* graphical illustration of the $^1$H NMR in CDCl$_3$ and the $^{13}$C NMR in CDCl$_3$ of the major and minor byproducts.

DETAILED DESCRIPTION

"Retention of epoxy groups" upon hydrogenation of an epoxy compound herein means a proportion of epoxy groups in the molecule that remain intact (i.e., not converted to other functional groups) after hydrogenation. This proportion may be expressed as a percentage, where 100% means that all the epoxy groups come though the transformation intact and 0% means that all the epoxy groups end up being destroyed.

A "low viscosity", with reference to a composition, herein means a viscosity of less than or equal to (≤) 1,500 mPa-s at 25° C.

A "low epoxy equivalent weight (EEW)", with reference to a composition, herein means an EEW of 201 g/equivalent or lower.

A "low total chlorine", with reference to a composition, herein means a concentration of ≤1 weight percent (wt %), preferably less than (<) 0.5 wt % and more preferably <0.3 wt % of chlorine present in the composition.

The cycloaliphatic epoxy resin of the present invention is a reaction product resulting from the hydrogenation of an epoxy resin in the presence of a catalyst and in the presence of a solvent.

As an illustration of one preferred example for producing the cycloaliphatic epoxy resin product of the present invention, the chemical reaction Scheme (II) which follows, shows a cycloaliphatic epoxy resin such as a cycloaliphatic diglycidyl ether produced via direct catalytic hydrogenation of a commercial bisphenol A diglycidyl ether.

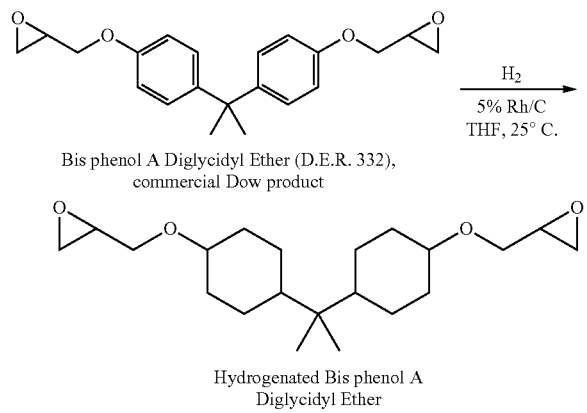

Scheme (II)

Bis phenol A Diglycidyl Ether (D.E.R. 332), commercial Dow product

Hydrogenated Bis phenol A Diglycidyl Ether

The epoxy compound useful as the epoxy starting material component to be hydrogenated by the process of the present invention is an aromatic compound having two or more epoxy groups and can be, for example, bisphenol A diglycidyl ether, bisphenol F diglycidyl ether, a phenol or cresol novolak type epoxy resin, hydroquinone diglycidyl ether, resorcinol diglycidyl ether, biphenol diglycidyl ether, 3,3',5,5'-tetramethylbiphenol diglycidyl ether, and mixtures thereof.

In one preferred embodiment, the epoxy compound starting material can be diglycidyl ethers, for example, bisphenol A diglycidyl ether, bisphenol F diglycidyl ether, or mixtures thereof.

In general, because it is desirable that the EEW targeted for the hydrogenated epoxy resin composition be as low as possible, the amount of the aromatic epoxy resin in the starting material to be hydrogenated is desired to be as high as possible; a pure 100% aromatic epoxy resin starting material is one preferred embodiment. For example, the amount of epoxy resin compound starting material useful in the present invention, may be an amount of epoxy compound sufficient to produce a final hydrogenated epoxy resin composition having an EEW of from 176.26 (½ MW) to about 201 in one embodiment, and from about 180 to about 195 in another embodiment. The EEW of the epoxy resin is the weight in grams of resin containing 1 mole equivalent of epoxide (g/equivalent).

The epoxy resin starting material concentration in a reaction solvent from about 10 wt % to about 50 wt % in one embodiment, and from about 30 wt % to about 40 wt % in another embodiment. If the concentration of the epoxy resin starting material in a solvent is higher than 50 wt %, the epoxy resin mixture is too viscous for a productive reaction; and if the concentration of the epoxy resin starting material in a solvent is lower than 10 wt %, a large reactor is required for the process to operate economically.

The catalyst compound useful in the process for hydrogenating the epoxy starting material component by the process of the present invention can be a heterogeneous catalyst containing a precious metal. The catalyst can be, for example, a rhodium metal, a ruthenium metal, alloys of ruthenium, alloys of rhodium, or mixtures thereof. A preferred embodiment of the catalyst includes a rhodium metal. The metal catalyst can be deposited onto a corresponding solid support. For example, the catalyst compound useful for the process of the present invention may include a metal catalyst such as for example rhodium (Rh) on a carbon support. Effective carbon supports that can be used in the present invention may include for example activated carbon, carbon nanotubes, and graphene. Other supports useful in the present invention may include for example alumina, silica or zeolites. A preferred embodiment for the catalyst support is activated carbon.

The percentage of Rh on the solid support can be generally from about 0.2 wt % to about 50 wt % in one embodiment, from about 0.5 wt % to about 30 wt % in another embodiment; and from about 2 wt % to about 10 wt % in still another embodiment.

The percentage of Rh dispersion can be generally a Rh dispersion of from about 10% to about 50%, from about 20% to about 45% in another embodiment, and from about 25% to about 35% in still another embodiment. "Dispersion" as used herein is defined as the percentage of active metal atoms in a supported metal catalyst that is exposed and available to catalyze a surface reaction.

In the present invention, the catalyst is solid and the pH of the catalyst cannot be directly measured. It is important, however, to maintain a pH of the catalyst measured as a suspension in water at or near a neutral pH. Water can be used in the present process as a media to measure catalyst acidity/basicity; however, preferably water is not used to carry out the hydrogenation reaction as described herein. Instead, anhydrous solvents are preferably used to carry out the hydrogenation reaction.

The pH of the catalyst is preferably measured as a 5 wt % suspension in water. For example, the pH of the catalyst as a 5 wt % suspension in water can be a pH of at least about 3 and up to <about 9 in one embodiment; at least about 4 and up to <about 8 in another embodiment; from about 5 and up to <about 7 in still another embodiment. The pH is important—if too acidic then the epoxy starting material is deleteriously affected and may cause the decomposition of the epoxy starting material and could possibly reduce the epoxy groups retention.

The support useful in the present invention may include for example activated carbon, zeolites, silica, alumina, or mixtures thereof. Preferably, the catalyst is deposited onto an activated carbon support.

A BET surface area of the support can generally for example at least 100 m²/g and up to about 1500 m²/g in one embodiment; at least about 200 m²/g and up to about 1200 m²/g in another embodiment; and at least about 400 m²/g and up to about 1000 m²/g in still another embodiment.

The mesopore area of the support generally can be for example, at least about 75 m²/g and up to about 750 m²/g in one embodiment; at least about 100 m²/g and up to about 500 m²/g in another embodiment; and at least about 200 m²/g and up to about 400 m²/g in still another embodiment.

In general the average particle size of the catalyst can be from about 0.5 nanometers (nm) to about 15 nm in one embodiment, from about 1 nm to about 10 nm in another embodiment, and from about 2 nm to about 9 nm in still another embodiment. In one preferred embodiment, the average Rh particle size can be in the range of from at least about 3 nm up to no more than about 8 nm.

The solvent used in the process of the present invention should be capable of dissolving the epoxy resin starting material and non-reactive with the components of the reaction mixture, i.e., inert to the hydrogenation reaction. The solvent compound useful in the process for hydrogenation process of the present invention can be for example ethers, hydrocarbons and combinations thereof.

In one preferred embodiment, the solvent useful in the present invention can be for example dioxane, tetrahydrofuran (THF), dibutylether, mixtures of THF with aliphatic hydrocarbons, and other mixtures thereof. The aliphatic hydrocarbons can include for example hexanes, heptanes, octanes and mixtures thereof.

Generally, the amount of solvent used in the present invention should be sufficient to allow for sufficient solubility of the starting aromatic epoxide. For example, a weight ratio of solvent to epoxy may be from 1 to about 10 in one embodiment, from about 2 to about 5 in another embodiment; and from about 2.5 to about 3 in still another embodiment. The use of a weight ratio of solvent above about 10 results in a very dilute solution, a requirement of large reactors for the process, and an inefficient system. The use of a weight ratio of solvent below about 1 results in a very viscous solution which makes the reaction it too difficult to be carried out.

Generally, the process for preparing the cycloaliphatic epoxy resin composition of the present invention via a hydrogenation reaction, includes dissolving at least one aromatic epoxy compound in a solvent at the appropriate concentrations, and optionally, any other optional ingredient as desired; and contacting the epoxy solution with the catalyst on a carbon support under a hydrogen pressure at a predetermined temperature and reaction time. The components of the reaction mixture are mixed at a sufficient mixing rate to provide a well-mixed uniform reaction mixture. For example the speed of mixing can be a rate of >800 rpm. Once the reaction is complete, the catalyst is preferably separated from the reaction product and solvent. For example the separation can be by standard filtering methods and equipment. The solvent/reaction product (having been separated from the catalyst) is then heated to separate/remove the solvent from the reaction product by evaporation leaving the product remaining after evaporation. The preparation of the cycloaliphatic epoxy resin composition of the present invention, and/or any of the steps thereof, may be a batch or a continuous process. The equipment employed to carry out the hydrogenation reaction includes equipment known to those skilled in the art.

The hydrogenation reaction is carried out at process conditions to enable the preparation of an effective cycloaliphatic epoxy resin composition having the desired balance of properties for a particular application. For example, generally, the hydrogenation reaction can be carried out at a hydrogen pressure of from about 350 kPa to about 17,200 kPa in one embodiment; from about 700 kPa to about 13,800 kPa in another embodiment; and from about 2,100 kPa to about 8,300 kPa in still another embodiment. If the hydrogenation reaction is carried out below the range of 350 kPa, the reaction may not proceed; and above a pressure range of 17,200 kPa there is the risk of a potential over-reduction with opening of the epoxy cycle.

The hydrogenation reaction can be carried out at a temperature of from about 0° C. to about 80° C. in one embodiment; from about 20° C. to about 40° C. in another embodiment; and from about 25° C. to about 35° C. in still another embodiment. Below a hydrogenation reaction temperature of about 0° C., the reaction is very slow; and above a hydrogenation reaction temperature of about 80° C., a deleterious amount of byproducts are produced during the hydrogenation reaction. The byproducts are formed upon the epoxy cycle hydrogenation resulting in the production of hydroxyl compounds which leads to a product having a high viscosity (e.g., a product with a viscosity of >1,500 mPa-s at 25° C.).

The reaction time of the hydrogenation reaction may be generally from about 1 hour to about 24 hours in one embodiment, and from about 3 hours to about 6 hours in another embodiment.

Upon producing the cycloaliphatic epoxy resin composition product by the above process, optionally, other conventional procedures and/or steps can be used in addition to or in combination with the present invention process. For example, a catalyst separation operation and/or a solvent evaporation operation can be used in the process.

The cycloaliphatic epoxy resin composition product prepared by the process of the present invention is a novel composition. For example, in one embodiment, the product of the present invention contains an isomeric mixture of Compound A having the following chemical structure A:

Compound A

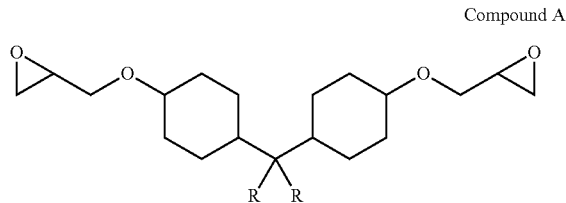

wherein R can be hydrogen (H) or a methyl group (CH₃); and Compound B having the following chemical structure B:

Compound B

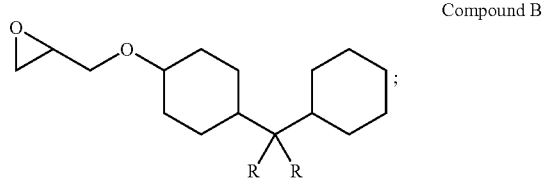

wherein R can be hydrogen (H) or a methyl group (CH$_3$).

In a preferred embodiment, the isomeric mixture product of the present invention may generally comprise at least about 85% of Compound A, at least about 90% of Compound A in another embodiment, and from about 90% to about 95% of Compound A in still another embodiment.

In one preferred embodiment, the isomeric mixture product of the present invention may generally comprise at least about 2% of Compound B, at least about 3% of Compound B in another embodiment, and from about 3% to about 10% of Compound B in still another embodiment.

A combined percentage of Compound A and Compound B in the isomeric mixture product of the present invention may generally be at least about 90% in one embodiment, >about 95% in another embodiment, and >about 97% in still another embodiment.

Compound B may consist of two isomers, cis (major) and trans (minor), each of the isomers is a new composition of matter. As an epoxy diluent, Compound B reduces viscosity of the material since Compound B does not contain hydroxyl groups. Known commercial products can contain a variety of impurities particularly impurities having hydroxyl groups; and such hydroxyl groups-containing impurities can possess a relatively high viscosity that tends to increase the total product viscosity and the total product epoxy equivalent weight when present in the product.

Another difference between the present invention product and the product of the known prior art includes, for example, the present invention employs a non-graphite catalyst support. The non-graphite catalyst support of the present invention is beneficial because the use of such catalyst allows for less catalyst deactivation upon reuse.

In addition, the advantages of the present invention include, for example, enhanced properties imparted to the product, in particular, product viscosity, which can be for example less than or equal to (≤) about 1,400 mPa-s at 25° C. Generally, the viscosity of the product of the present invention can be from about 400 mPa-s to about 1,400 mPa-s in one embodiment, from about 500 mPa-s to about 900 mPa-s in another embodiment, and from about 600 mPa-s to about 800 mPa-s in still another embodiment at 25° C. In turn, because the product has a low viscosity, the product can be used without using solvents or diluents for the sole purpose of reducing the viscosity of the product. The product of the present invention is easily processed and readily handled in the hydrogenation process to form the product, that is, the processability of the resin product of the present invention is improved compared to known products disclosed in the prior art.

Another embodiment of the present invention is directed to a curable resin formulation or composition including (I) the cycloaliphatic epoxy resin composition product as described above; and (II) at least one curing agent compound. Other optional additives known to the skilled artisan can be included in the curable composition such as for example a curing catalyst and other additives for various enduse applications.

The curable composition of the present invention may include the cycloaliphatic epoxy resin composition product as described above as component (I) to form the epoxy matrix in a final curable composition or formulation. The curable formulation can be cured to form a cured product or thermoset such as a cured coating film.

Generally, the amount of the cycloaliphatic epoxy resin composition product used in the curable composition of the present invention will depend on the enduse of the curable composition. The amount of the epoxy resin used to prepare the curable composition can be measured in terms of molecular equivalent. For example, as one illustrative embodiment, when the curable composition is used to prepare a coating, the concentration of cycloaliphatic epoxy resin composition product can be generally from about 0.7 molar equivalent to about 2 molar equivalents in one embodiment, from about 0.8 molar equivalent to about 1.5 molar equivalent in another embodiment; and from about 0.9 molar equivalents to about 1.4 molar equivalent in still another embodiment; based on the moles of active amine hydrogen in the curing agent of the curable composition. If the composition of the thermosetting epoxy compound is outside the above listed ranges, the thermosetting epoxy compound will either be present in significant excess or depletion, which creates coatings that will not be fully cured and will have poor final coating properties.

In general, the curing agent (also referred to as a hardener or crosslinking agent), component (II), is blended with the cycloaliphatic epoxy resin composition, component (I), to prepare the curable composition or formulation. The curable formulation can be cured to form a cured product or thermoset such as a cured coating film.

Generally, the amount of the curing agent used in the curable composition of the present invention will depend on the enduse of the curable composition. For example, as one illustrative embodiment, when the curable composition is used to prepare a coating, the molar equivalence of active hydrogen of curing agent composition can be generally from about 0.5 molar equivalents to about 1.5 molar equivalents in one embodiment, from about 0.6 molar equivalents to about 1.3 molar equivalents in another embodiment; and from about 0.7 molar equivalents to about 1.1 molar equivalents in still another embodiment; based on the moles of epoxy of the curable composition. If the composition of the thermosetting epoxy compound is outside the above listed ranges, the curing agent will either be present in significant excess or depletion, which creates coatings that will not be fully cured and will have poor final coating properties.

In preparing the curable resin formulation of the present invention, optional compounds may be used including for example one of the components of the formulation can be at least one cure catalyst to facilitate the reaction of the epoxy resin compound with the curing agent. The catalyst useful in the present invention may include for example, ethyl p-toluene sulfonic acid; glycerin; benzyl alcohol; 2,4,6-tris(dimethylaminomethyl)phenol (DMP-30); salicylic acid; or any combination thereof.

Generally, the amount of cure catalyst when used in the curable composition may be for example, from 0 wt % to about 70 wt % in one embodiment, from about 0.01 wt % to about 30 wt % in another embodiment; and from about 0.1 wt % to about 10 wt % in still another embodiment.

Other optional compounds that may be added to the curable composition of the present invention may include compounds that are normally used in resin formulations known to those skilled in the art for preparing curable compositions and thermosets. For example, the optional components may comprise compounds that can be added to the composition to enhance application properties (e.g., surface tension modifiers or flow aids), reliability properties (e.g., adhesion promoters) the reaction rate, the selectivity of the reaction, and/or the catalyst lifetime.

Other optional compounds that may be added to the curable composition of the present invention may include, for example, de-molding agents; other accelerators a solvent to lower the viscosity of the formulation further, other resins such as a phenolic resin or aliphatic epoxy resins or aromatic epoxy resins that can be blended with the other ingredients in the curable formulation, other curing agents, fillers, pigments, toughening agents, flow modifiers, adhesion promoters, diluents, stabilizers, plasticizers, catalyst de-activators, flame retardants, and mixtures thereof. The amount of additives added are dependent on the application and is commonly known to those practiced in the art of formulating curable compositions.

The process for preparing the curable composition of the present invention includes admixing (I) the cycloaliphatic epoxy resin composition product as described above; (II) at least one curing agent compound; and (III) optionally, any other optional ingredients as desired. For example, the preparation of the curable resin formulation of the present invention is achieved by blending, in known mixing equipment, the cycloaliphatic epoxy resin composition product, the curing agent, and optionally any other desirable additives. Any of the above-mentioned optional additives, for example a curing catalyst, may be added to the composition during the mixing or prior to the mixing to form the composition.

All the compounds of the curable formulation are typically mixed and dispersed at a temperature enabling the preparation of an effective curable epoxy resin composition having the desired balance of properties for a particular application. For example, the temperature during the mixing of all components may be generally from about −10° C. to about 40° C. in one embodiment, and from about 0° C. to about 30° C. in another embodiment. Lower mixing temperatures help to minimize reaction of the epoxide and hardener in the composition to maximize the pot life of the composition.

The preparation of the curable formulation of the present invention, and/or any of the steps thereof, may be a batch or a continuous process. The mixing equipment used in the process may be any vessel and ancillary equipment well known to those skilled in the art.

The process of the present invention includes curing the curable resin composition to form a thermoset or cured composition. The process of curing of the curable composition may be carried out at a predetermined temperature and for a predetermined period of time sufficient to cure the composition and the curing may be dependent on the hardeners used in the formulation. For example, the temperature of curing the formulation may be generally from about 10° C. to about 200° C. in one embodiment; and from about 100° C. to about 190° C. in another embodiment. Generally, the curing time for the process of curing the curable composition may be chosen between about 1 minute to about 4 hours in one embodiment, between about 5 minutes to about 2 hours in another embodiment, and between about 10 minutes to about 1.5 hours in still another embodiment. Below a period of time of about 1 minute, the time may be too short to ensure sufficient reaction under conventional processing conditions; and above about 4 hours, the time may be too long to be practical or economical.

In general, the curable composition of the present invention may be used to manufacture a cured thermoset product for various applications. The cured hydrogenated liquid epoxy resin composition product (i.e., the cross-linked product made from the curable composition) of the present invention shows several improved properties over conventional epoxy cured resins. For example, the cured product of the present invention may advantageously have better properties such as improved reactivity due to higher volume normalized functionality; and improved light stability.

The beneficial properties of the cured product can be measured and determined based on the end use for which the cured product will be used. For example, when the epoxy resin composition or formulation of the present invention is used for preparing a coating, the cured coating product can exhibit a combination, i.e., a balance, of advantageous properties including for example processability, Tg, mechanical performance and weatherability (i.e., outdoor light stability).

In another embodiment, a low volatile organic compounds (VOC) coating can be prepared by curing the hydrogenated liquid epoxy resin composition product with a curing agent such an amine hardener such that the resulting product exhibits better properties compared to aliphatic commercial resins such as Epalloy 5000, especially with respect to the product's chemical resistance property. For example, the chemical resistance of the present invention cured coatings product can be measured by the 24-hour spot test method described in ASTM D-1308. Generally, the relative chemical resistance of the cured product can be determined using a scale from "1" to "5" wherein "5" is the best chemical resistance showing no visible effect and "1" is the worst chemical resistance showing severe blistering, cracking, dissolving of material. The product of the present invention generally exhibits a chemical resistance of from about 5 to about 2 in one embodiment, from about 5 to about 3 in another embodiment, and from about 5 to about 4 in still another embodiment. Regarding a low VOC coating prepared in accordance with the present invention, a low VOC or zero VOC coating can be obtained since the coatings of the present invention can be prepared in the absence of solvents.

While not intended to be limited thereby, it is hypothesized that the improved chemical resistance of the present invention coatings may be due to increased specific density of epoxy groups in the hydrogenated epoxy resin material (e.g., h-LER 332), with less impurities in the epoxy resin useful in the present invention and with a lower epoxy equivalent weight. This creates a robust and dense cross-linking network upon curing and is more resistant to aggressive agents.

EXAMPLES

The following examples and comparative examples further illustrate the present invention in detail but are not to be construed to limit the scope thereof.

Various terms and designations used in the following examples are explained herein below:

"THF" stands for tetrahydrofuran.
"GC" stands for gas chromatography.
"LC" stands for liquid chromatography.
"MS" stands for mass spectrometry.
"NMR" stands for nuclear magnetic resonance.
"Bisphenol A DGE" stands for bisphenol A diglycidyl ether.
"CDC13" stands for deuterated chloroform.
D.E.R. 331 is an epoxy resin based on bisphenol A diglycidyl ether with epoxy equivalent weight of 182-192 g/eq and a viscosity of 11,000-14,000 mPa·s at 25° C.; commercially available from The Dow Chemical Company.
D.E.R. 332 is an epoxy resin based on bisphenol A diglycidyl ether with epoxy equivalent weight of 171-175 g/eq and a viscosity of 4,000-6,000 mPa·s at 25° C.; commercially available from The Dow Chemical Company.
D.E.R. 354 is an epoxy resin based on bisphenol F diglycidyl ether with epoxy equivalent weight of 167-174 g/eq and a viscosity of 3,400-4,200 mPa·s at 25° C.; commercially available from The Dow Chemical Company.

Epalloy® 5000 is a hydrogenated bisphenol A diglycidyl ether based epoxy resin commercially available from CVC Thermoset Specialties Company.

Polypox™ H013 is an accelerated Mannich base hardener with an amine hydrogen equivalent weight (AHEW) of 90 commercially available from UPPC, a wholly owned subsidiary of The Dow Chemical Company.

D.E.H. 24 is an aliphatic polyamine hardener (triethylenetetraamine) commercially available from The Dow Chemical Company.

The following standard analytical equipment and methods are used in the Examples Viscosity: For example, a Brookfield CAP2000+ viscometer is used to measure the viscosity of the curable composition after the composition is mixed. The viscosity is recorded as a function of time. Pot life (in minutes) is the time it took for the initial viscosity of a composition to double.

Mandrel Bend Flexibility: Flexibility is measured using the method described in ASTM D-522 (2008) and using a BYK Gardner Conical Mandrel Bending Tester, PF-5750 (BYK-Gardner USA). The coatings are bent around the small diameter end of the tester (3.175 mm to 20 mm) from the largest dimension to the smallest, and the largest diameter that fails is reported.

Impact Resistance: Impact resistance is measured using the method described in ASTM D-2794 (2010) and using a Gardner dart falling weight impact tester (PF-1125, BYK Gardner Inc.). The maximum impact force; and the product of the weight of the dart and maximum falling distance without creating a crack or delamination; is reported.

Cross Hatch Adhesion: A cross hatch adhesion test is performed using the method described in ASTM D-3359 (2009) and a BYK Gardner tester. The results of the adhesion test is rated on a scale of from "5B" to "1B" with the rating "5B" being perfect adhesion and the rating "1B" being poor adhesion.

Hardness: A Fischer microindenter (Helmut-Fischer Fischerscope™ HM2000 XYp, Fischer Technology, Inc.) is used to apply a 5 mN load on a coating at a rate of 0.25 mN/second. The indenter tip of the microindenter is then held at the maximum load for 5 seconds before retracting the indenter tip at the same load decrease rate. Martens hardness is reported using the above hardness test.

Dry Time: A Dry Time Recorder (BYK Instruments) is used to determine the drying speed of the coating mixture. The procedure described in ASTM D5895 is followed for the drying time test. The test includes casting coatings onto glass substrates. The glass substrates are typical soda lime glass (30 cm in length×0.22 cm in width×0.2 cm in thickness). Prior to coating the glass substrates, the glass substrates are cleaned with isopropanol. The coatings are applied by using a film applicator and holder (BYK Instruments). The drawdown cap (wet thickness) is 76 micron. Testing is done within a ventilated hood at ambient temperature. After the coatings are applied to the glass substrates, the following four dry stages are determined during the testing: (1) set-to-touch time, (2) tack-free time, (3) dry-hard time, and (4) dry-through time.

Chemical Resistance: A chemical resistance test is performed on the coating panels according to the procedure described in ASTM D-1308. The coating panels are laid out at room temperature (about 25° C.) and the chemicals are placed as spots on the coating for 24 hours with a cover over each droplet to inhibit evaporation. After the 24-hour exposure time, the covers are removed from the coating panel, the chemicals are rinsed off, and the coating panel is patted dry with a clean cloth. The panel is observed and rated for whitening and obvious changes in coating appearance. A rating on a scale value of from "1" to "5" is used to determine the chemical resistance of the coating wherein 5 means there is nothing visible on the coating and wherein 1 means the coating exhibited severe damage visible to the eye.

Example 1—Hydrogenation of D.E.R. 332, Bisphenol A DGE

D.E.R. 332 (51.0 g; 150 mmol) with an epoxy equivalent weight of 172.6 was dissolved in THF (100 mL) and then the dissolved material was charged into a 250 mL Parr reactor containing 5.0 g of 5% Rh/C (2.5 mmol Rh). The resultant mixture was purged with hydrogen three times at 700 kPa. Hydrogenation was carried out at 8,300 kPa of hydrogen and room temperature. After about 1 hour (hr) the temperature rose to 35° C. and the reactor was cooled with cold water to bring the temperature to 25° C. The reaction was followed by GC. After 3 hr, the reaction mixture showed three new major peaks with retention times in the range 23-29 minutes (min) accounting for 89.9 GC area %. The reaction mixture was filtered, and the catalyst washed with THF (80 mL×2), which was combined with the filtrate. Then THF was evaporated to give the hydrogenated product quantitatively. $^1$H NMR analysis revealed only 0.5% residual aromatics (99.5% hydrogenation extent). The measured epoxy equivalent weight was 192 g/eq.

Example 2—Hydrogenation of D.E.R. 331, Bisphenol A DGE

D.E.R. 331 (30.6 g; 90 mmol) with an epoxy equivalent weight of 186 was dissolved in THF (100 mL) and then the dissolved material was charged in a 150 mL Parr reactor containing 3.0 g of 5 Rh/C (1.5 mmol Rh). The resultant mixture was purged with hydrogen three times at 700 kPa. Hydrogenation was carried out at 8,300 kPa of hydrogen and room temperature. After about 1 hr the temperature rose to 35° C. and the reactor was cooled with cold water to bring the temperature to 25° C. The reaction was followed by GC. After 6 hr, the reaction mixture showed three new major peaks with retention times in the range 23-29 min accounting for 88.5 GC area %. The reaction mixture was filtered, and the catalyst washed with THF (30 mL×2), which was combined with the filtrate. Then THF was evaporated to give the hydrogenated product quantitatively. $^1$H NMR analysis revealed only 0.4% residual aromatics (99.6% hydrogenation extent). The measured epoxy equivalent weight was 201 g/eq.

Example 3—Hydrogenation of D.E.R. 354, Bisphenol F DGE

D.E.R. 354 (16.3 g; 50 mmol) with an epoxy equivalent weight of 170 was dissolved in anhydrous THF (33 mL) and then the dissolved material was charged in a 150 mL Parr reactor containing 1.0 g of 5% Rh/C (0.5 mmol Rh). The resultant mixture was purged with hydrogen three times at 700 kPa. Hydrogenation was carried out at 8,300 kPa of hydrogen and 60° C. The reaction was followed by GC. After 3 hr, $^1$H NMR analysis revealed 0.7% residual aromatics (99.3% hydrogenation efficiency). The reaction mixture was filtered, and the catalyst washed with THF (20 mL×2), which was combined with the filtrate. Then THF was evaporated to give the hydrogenated product quantitatively. The measured epoxy equivalent weight was 191 g/eq.

Example 4—Hydrogenation of Low Chlorine Bisphenol A DGE

Commercial solid bisphenol A DGE from Aldrich containing 1920 ppm of total chlorine was purified using the procedure from U.S. Patent Application Publication No. 2009/0286951 to reduce the total chlorine content to 260 ppm. The low chlorine, purified bisphenol A DGE (20.4 g; 60 mmol) with the epoxy equivalent weight of 170 was dissolved in THF (40 mL) and charged in a 150 mL Parr reactor containing 2.0 g of 5% Rh/C (1.0 mmol Rh). The resultant mixture was purged with hydrogen three times at 700 kPa. Hydrogenation was carried out at 8,300 kPa of hydrogen and room temperature. The reaction was followed by GC. After 6 hr, the reaction mixture showed three new major peaks with retention times in the range of 23-29 min. The reaction mixture was filtered, and the catalyst washed with THF (20 mL×2), which was combined with the filtrate. Then THF was evaporated to give the hydrogenated product quantitatively. $^1$H NMR analysis revealed only 0.2% residual aromatics (99.8% hydrogenation extent). The measured epoxy equivalent weight was 182.6 g/eq.

Example 5

In this Example 5, the chemical components of a hydrogenated liquid epoxy resin composition were determined; and the Compound B byproducts of said epoxy resin composition were isolated and the structure of the Compound B byproducts was elucidated by NMR and MS.

Figure 1:
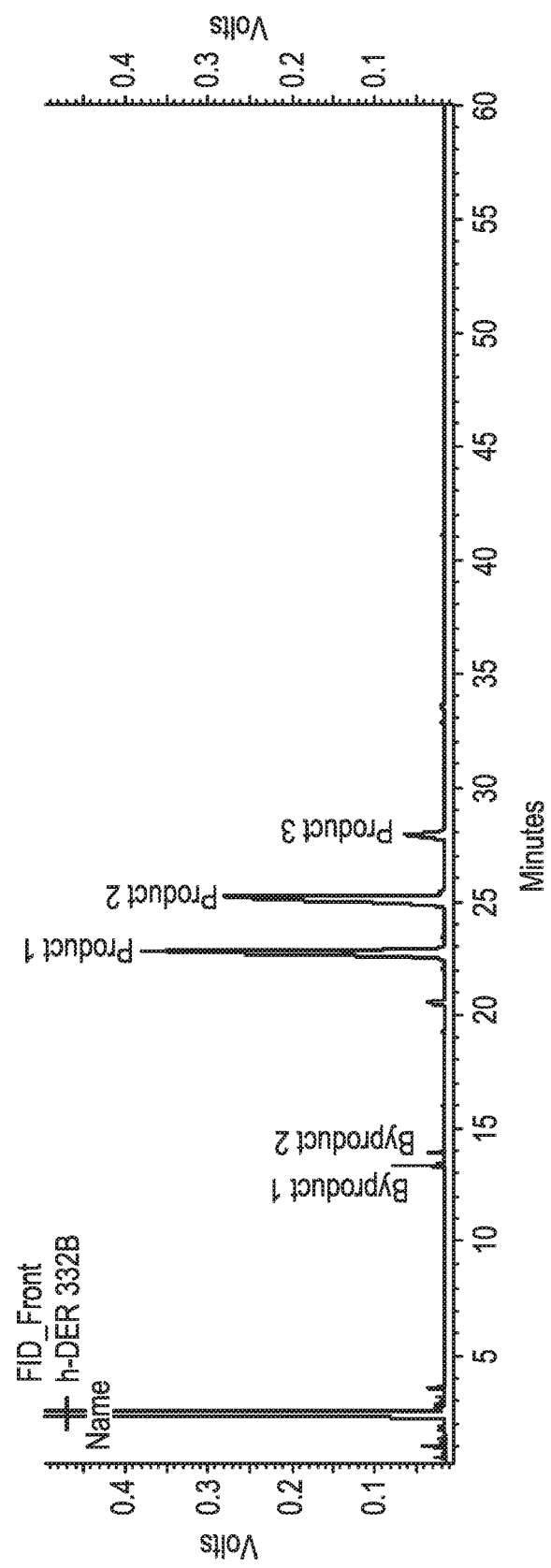
FIG. 1 is graphical illustration of a gas chromatography scan of a product mixture, containing three isomers for product and two isomers for byproduct. Chemical structures for the product and the byproduct are as follows.

The epoxy resin composition from Example 1 was analyzed by GC/MS and LC/MS. FIG. 1 illustrates a typical GC scan of the epoxy resin composition.

Three major isomers of the Compound A product (Compound A isomers, as shown in FIG. 2) present in the epoxy resin composition were isolated by column chromatography on silica gel using hexane-ethyl acetate 20:1. Each of the structures of the isolated isomers was characterized by $^1$H and $^{13}$C NMR (as shown in FIGS. 3 and 4) and for one isomer by X-ray crystallography (as shown in FIG. 5).

Two byproducts (Compound B isomers, as shown in FIG. 2) present in the epoxy resin composition, which are new compositions of matter, were also identified by GC/MS and LC/MS, isolated by column chromatography, and characterized by NMR. The assignment of each Compound B isomer was done using $^{13}$C NMR chemical shift relationship between the ring carbon connected to the axial and equatorial group, respectively. The chemical shift for the trans isomer (equatorial configuration) is always higher than for the cis isomer (axial configuration) according to the literature (*Magn. Resonance Chem.* 1986, 792; *J. Am. Chem. Soc.* 1987, 109, 198; *J. Am. Chem. Soc.* 1987, 109, 225).

The chemical structures of the major and minor byproducts are shown as follows:
Major Byproduct Isomer (cis):

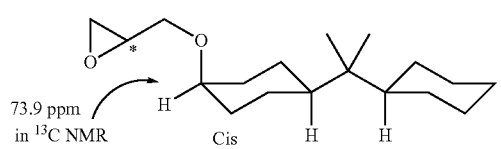 [SMILES: CC(C)(C1CCCCC1)C1CCC(OCC2CO2)CC1]

Minor Byproduct Isomer (trans):

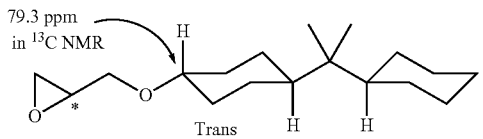 [SMILES: CC(C)(C1CCCCC1)C1CCC(OCC2CO2)CC1]

The $^1$H NMR in CDCl$_3$ and the $^{13}$C NMR in CDCl$_3$ of the major and minor byproducts described above are shown in FIGS. 5a and 5b; and in FIGS. 6a and 6b, respectively.

Viscosity: Examples 1 to 4 and Comparative Examples A to F

A viscosity comparison among the hydrogenated epoxy resins and their aromatic counterparts was carried out. The viscosity of the compositions was determined using an Ares II liquids analyzer in a temperature step program from −40° C. to 40° C. in a cup and plate geometry. Frequency was constant at 6.2 radians/second (rads/sec) and Strain % varied from 0.015% at −40° C. to approximately 30% at 40° C. The data described in Table I provides a viscosity comparison at 25° C.

TABLE I

| Example | Epoxy Resin | Viscosity (mPa · s) |
|---|---|---|
| Comparative Example A | D.E.R. 332 | 22,400 (solidifies on standing) |
| Comparative Example B | D.E.R. 331 | 11,000-14,000* |
| Comparative Example C | D.E.R. 354 | 3,400-4,200* |
| Comparative Example D | Low Cl Bisphenol A DGE** | Solid |
| Comparative Example E | Epalloy 5000 | 2,600 |
| Comparative Example F | Eponex 1510 | 2,700 |
| Example 1 | Hydrogenated DER 332 | 980 |
| Example 2 | Hydrogenated DER 331 | 1,400 |
| Example 3 | Hydrogenated DER 354 | 420 |
| Example 4 | Hydrogenated Low Cl Bisphenol A DGE | 440 |

*Published value
**As described in Example 4

Example 6-9 and Comparative Example G-L: Curable Composition and Coatings

Coatings were prepared using the epoxy resins from the above Comparative Examples and from the Examples above with two different curing agents, and the compositions are listed in Table II.

TABLE II

| Curable Compositions | | |
|---|---|---|
| Example | Epoxy Resin | Curing Agent |
| Comparative Example G | Comparative Example A | Polypox H013 |
| Comparative Example H | Comparative Example B | Polypox H013 |

TABLE II-continued

Curable Compositions

| Example | Epoxy Resin | Curing Agent |
|---|---|---|
| Comparative Example I | Comparative Example C | Polypox H013 |
| Comparative Example J | Comparative Example E | Polypox H013 |
| Example 6 | Example 1 | Polypox H013 |
| Example 7 | Example 3 | Polypox H013 |
| Comparative | Comparative | DEH 24 |

TABLE II-continued

Curable Compositions

| Example | Epoxy Resin | Curing Agent |
|---|---|---|
| Example K | Example A | |
| Comparative Example L | Comparative Example B | DEH 24 |
| Comparative Example M | Comparative Example C | DEH 24 |
| Comparative Example N | Comparative Example E | DEH 24 |
| Example 8 | Example 1 | DEH 24 |
| Example 9 | Example 3 | DEH 24 |

Each of the above products were mixed, using a dual axis mixer (SpeedMixer, Model # DAC 150 FVZ-K, FlackTek Inc.), at ambient temperature (22° C.) for 2 min at 2000 revolutions per minute (rpm) with Polypox™ H013 and triethylene tetraamine (DEH 24) at a 1:1 epoxy to amine equivalent ratio. Then the mixtures were tested for resin and coating properties.

The coating compositions were tested for pot life (2× of initial viscosity). The measured coating film properties are as indicated in Table III. To prepare the coating, the coating composition was applied and drawn down with a wire wound rod to a cold rolled steel substrate to give a film having a dry-film thickness of 50 μm. The coatings were allowed to dry at ambient temperature for 14 days prior to testing the coatings.

The coatings were tested for dry time (set to touch and tack free), hardness, cross hatch adhesion, impact resistance, mandrel bend flexibility, and chemical resistance. The results are shown in Table III. Coatings made from Examples 6 and 7 exhibited a longer pot life and a slower dry time (about 2× slower) than the Comparative Examples G and I. However, coatings made from Examples 6, 7, 8 and 9 exhibited a better cross hatch adhesion, impact resistance and flexibility than the aromatic commercial products (Comparative Examples G, I, K and M). In general, the coatings made of Examples 6, 7, 8 and 9 using the hydrogenated resins (Examples 1 and 3) have better mechanical properties and processability properties than the comparative products.

TABLE III

Curable Composition and Coating Properties

| Example | Flexibility* (cm) | Impact Resistance (J) | cross hatch adhesion | Hardness (mN/mm$^2$) | Set to touch (hr) | Tack free (hr) | Pot Life (min) |
|---|---|---|---|---|---|---|---|
| Comparative Example G | 20 | 0.0 | 1B | 199 | 1 | 1.8 | 6.6 |
| Comparative Example I | 20 | 0.0 | 1B | 188 | 0.8 | 1.7 | 5.9 |
| Comparative Example J | 20 | 3.5 | 3B | 141 | 1.2 | 2.6 | 8.7 |
| Example 6 | 0 (pass) | 3.7 | 4B | 170 | 1.8 | 3.4 | 8.0 |
| Example 7 | 0 (pass) | 3.2 | 3B | 152 | 2.1 | 3.6 | 9.6 |
| Comparative Example K | 20 | 1.0 | 1B | 175 | — | — | — |
| Comparative Example M | 20 | 3.1 | 2B | 174 | — | — | — |
| Comparative Example N | 5 | 6.2 | 1B | 128 | — | — | — |
| Example 8 | 0 (pass) | 8.5 | 5B | 140 | — | — | — |
| Example 9 | 0 (pass) | 7.1 | 3B | 119 | — | — | — |

*the larger the number, the worse the flexibility.
"pass" means no crack observed through the diameter range The chemical resistance of coatings made Examples in Table II was tested and the some results are shown in Table IV. They show that h-LER 332 (Example 6 and 8) had superior chemical resistance when compared to aromatic epoxy resins and commercial incumbent Epalloy 5000 with the curing agents Polypox H013 and DEH 25.

TABLE IV

Chemical Resistances*

| Example | Brake Fluid | MEK | 10% NaOH | 10% Sulfuric Acid | 50% Ethanol | 10% Acetic Acid |
|---|---|---|---|---|---|---|
| Comparative Example G | 3 | 3 | 5 | 5 | 5 | 5 |
| Comparative Example H | 3 | 3 | 5 | 5 | 5 | 5 |
| Comparative Example J | 3 | 5 | 5 | 5 | 5 | 4 |
| Example 6 | 5 | 4 | 5 | 5 | 5 | 4 |
| Comparative Example K | 5 | 5 | 5 | 1 | 5 | 5 |
| Comparative Example L | 5 | 5 | 5 | 5 | 5 | 3 |
| Comparative Example N | 5 | 5 | 5 | 3 | 5 | 1 |
| Example 8 | 5 | 5 | 5 | 5 | 5 | 5 |

*The numerical ranking of 1 to 5 in this table indicates range of chemical resistance where 5 is best and 1 is worst.

The invention claimed is:

1. A composition comprising a hydrogenated epoxy compound having the following chemical formula B:

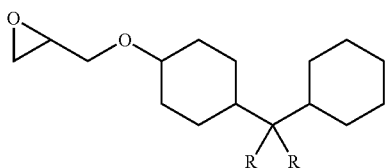

Compound B wherein R is hydrogen or CH$_3$.

2. The composition of claim 1, wherein the hydrogenated epoxy Compound B comprises cis- and trans-isomers.

3. The composition of claim 1 in which Compound B is a diluent.

4. An epoxy resin composition comprising an admixture of:
(A) a hydrogenated epoxy resin product having the following chemical formula A:

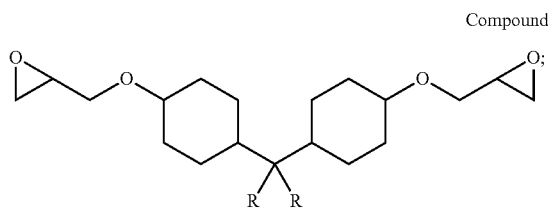

Compound A wherein R is hydrogen or CH$_3$; and
(B) a hydrogenated epoxy resin byproduct having the following chemical formula B:

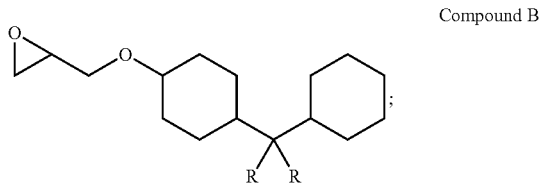

Compound B wherein R is hydrogen or CH$_3$; and wherein the viscosity of the epoxy resin composition is less than about 1,500 mPa-s.

5. The composition of claim 4, wherein the epoxy resin composition has a viscosity of from about 400 mPa-s to about 1,450 mPa-s.

6. The composition of claim 4, wherein the concentration of the hydrogenated epoxy resin product, component (A), is from about 85 weight percent to about 95 weight percent; and wherein the concentration of the hydrogenated epoxy resin byproduct, component (B), is from about 2 weight percent to about 10 weight percent.

7. The composition of claim 4, wherein the hydrogenated epoxy resin product, component (A), includes at least three isomers of the hydrogenated epoxy resin product, wherein the at least three isomers of the hydrogenated epoxy resin product include a cis-cis isomer, a cis-trans isomer, and a trans-trans isomer, and wherein the relative amounts of the at least three isomers of the hydrogenated epoxy resin product decrease in a sequence of cis-cis isomer greater than cis-trans isomer greater than trans-trans isomer.

8. The composition of claim 4, wherein the hydrogenated epoxy resin byproduct, component (B), includes at least two isomers of the byproduct, wherein the at least two isomers of the byproduct include a cis isomer and a trans isomer, wherein the relative amounts of the at least two isomers of the byproduct decrease in the sequence: cis isomer greater than trans isomer, and wherein the concentration of the byproduct is less than about 10 weight percent.

9. The composition of claim 4, wherein the hydrogenated epoxy resin product, component (A), is a diglycidyl ether of hydrogenated bisphenol A.

* * * * *